US008906414B1

(12) United States Patent
Shytle et al.

(10) Patent No.: US 8,906,414 B1
(45) Date of Patent: Dec. 9, 2014

(54) METHODS AND COMPOSITIONS FOR IMPROVING BIOAVAILABILITY OF EPIGALLOCATECHIN GALLATE (EGCG)

(75) Inventors: Roland Douglas Shytle, Largo, FL (US); Jun Tan, Tampa, FL (US); Adam Smith, Lutz, FL (US); Brian Giunta, Tampa, FL (US); Cyndy Davis Sanberg, Spring Hill, FL (US)

(73) Assignees: University of South Florida, Tampa, FL (US); Natura Therapeutics, Inc., Tampa, FL (US)

( * ) Notice: Subject to any disclaimer, the term of this patent is extended or adjusted under 35 U.S.C. 154(b) by 0 days.

(21) Appl. No.: 12/768,380

(22) Filed: Apr. 27, 2010

Related U.S. Application Data

(60) Provisional application No. 61/173,058, filed on Apr. 27, 2009, provisional application No. 61/172,970, filed on Apr. 27, 2009.

(51) Int. Cl.
*A61K 9/14* (2006.01)
*A61K 9/127* (2006.01)

(52) U.S. Cl.
USPC .......................................... 424/489; 424/450

(58) Field of Classification Search
USPC .................................................. 424/489, 450
See application file for complete search history.

(56) References Cited

U.S. PATENT DOCUMENTS

| | | | |
|---|---|---|---|
| 5,391,568 A | 2/1995 | Chung | |
| 5,804,567 A | 9/1998 | Cheng et al. | |
| 5,807,564 A | 9/1998 | Shimamura et al. | |
| 5,843,891 A | 12/1998 | Sherman | |
| 6,168,795 B1 | 1/2001 | DJang | |
| 6,383,392 B1 | 5/2002 | Bonrath et al. | |
| 7,014,876 B2 | 3/2006 | Iwasaki et al. | |
| 7,166,435 B2 | 1/2007 | Rosenbloom | |
| 7,270,840 B2 | 9/2007 | Lines et al. | |
| 7,452,549 B2 | 11/2008 | Hasler-Nguyen et al. | |
| 2007/0154539 A1 | 7/2007 | Fountain | |

OTHER PUBLICATIONS

Fang et al. J. Dermatol. Sci. 2006, 42, 101-109.*
Obregon et al. J. Biol. Chem. 2006, 281 (24), 16419-16427 (in IDS submitted Oct. 6, 2010).*
Hashimoto et al. Biosci. Biotechnol. Biochem. 1999, 63 (12), 2252-2255.*
Smith et al. 2010. "Nanolipidic Particles Improve the Bioavailability and Alpha-Secretase Inducing Abaility of Epigallocatechin-3-Gallate (EGCG) for the Treatment of Alzheimer's Disease." International Journal of Pharmaceutics. vol. 389. pp. 207-212.
Singh et al. 2003. "Epigallocatechin-3-Gallate Selectively Inhibits Interleukin1beta-Induced Activation of Mitogen Activated Protein Kinase Subgroup C-Jun N-Terminal Kinase in Human Osteoarthritis Chondrocytes." J. Orthop. Res. vol. 21. No. 1. pp. 102-109.
Katiyar et al. 1999. "Polyphenolic Antioxidant (−)-Epigallocatechin-3-Gallate from Green Tea Reduces UVB-Induced Inflammatory Responses and Infiltration of Leukocytes in Human Skin." Photochem. Photobiol. vol. 69. No. 2. pp. 148-153.
Lambert et al., Epigallocatechin-3-Gallate Is Absorbed but Extensively Glucuronidated Following Oral Administration to Mice, The Journal of Nutrition, 2003, vol. 133, pp. 4172-4177.
Lambert et al., Piperine Enhances the Bioavailability of the Tea Polyphenol (−)-Epigallocatechin-3-Gallate in Mice, The Journal of Nutrition, 2004, vol. 134, pp. 1948-1952.
Lambert et al., Short Communication, Dose-Dependent Levels of Epigallocatechin-3-Gallate in Human Colon Cancer Cells and Mouse Plasma and Tissues, Drug Metabolism and Disposition, 2006, vol. 34, No. 1, pp. 8-11.
Lambert et al., Peracetylation as a Means of Enhancing in Vitro Bioactivity and Bioavailability of Epigallocatechin-3-Gallate, Drug Metabolism and Disposition, 2006, vol. 34, No. 12, pp. 2111-2116.
Obregon et al., ADAM10 Activation Is Required for Green Tea (−)-Epigallocatechin-3-Gallate-Induced Alpha-Secretase Cleavage of Amyloid Precursor Protein, The Journal of Biological Chemistry, 2006, vol. 281, No. 24, pp. 16419-16427.
Cai et al., Contribution of Presystemic Hepatic Extraction to the Low Oral Bioavailability of Green Tea Catechins in Rats, Drug Metabolism and Disposition, 2002, vol. 30, No. 11, pp. 1246-1249.
Chow et al., Phase I Pharmacokinetic Study of Tea Polyphenols Following Single-Dose Administration of Epigallocatechin Gallate and Polyphenon E, Cancer Epidemiology, Biomarkers & Prevention, 2001, vol. 10, pp. 53-58.
Ghafouri et al., HIV-I Associated Dementia: Symptoms and Causes, Retrovirology, 2006, vol. 3, No. 28, pp. 1-11.
Henning et al., Nongallated Compared with Gallated Flavan-3-ols in Green and Black Tea are More Bioavailable, The Journal of Nutrition, 2008, vol. 138, pp. 1529S-1534S.
Zhang et al., Investigation of Intestinal Absorption and Disposition of Green Tea Catechins by Caco-2 Monolayer Model, International Journal of Pharmaceutics, 2004, vol. 287, pp. 1-12.
Zutshi et al., Influence of Piperine on Rifampicin Blood Levels in Patients of Pulmonary Tuberculosis, J. Assoc. Physicians India, 1985, vol. 33, No. 3, pp. 223-224.

(Continued)

*Primary Examiner* — Gina C Justice
*Assistant Examiner* — Genevieve S Alley Gsa
(74) *Attorney, Agent, or Firm* — Michele L. Lawson; Smith & Hopen, P.A.

(57) ABSTRACT

Compositions and methods of increasing the bioavailability of catechins are presented. Compositions for increasing the bioavailability of catechins include compositions where the catechin is added to a solution of ethanol and water; compositions where the catechin is encapsulated within a nanoparticle; and compositions in which a nanoparticle complex is formed between the catechin and the nanoparticle. Each of these compositions was shown to increase bioavailability of EGCG and is useful in treating diseases such as Alzheimer's and HIV-associated dementia.

12 Claims, 4 Drawing Sheets

(56) References Cited

OTHER PUBLICATIONS

Wang et al., Multi-Component Plasma Quantitation of Anti-Hyperglycemic Pharmaceutical Compounds Using Liquid Chromatography-Tandem Mass Spectrometry, Journal of Chromatography B, 2007, vol. 856, pp. 318-327.
Wissing et al., Solid Lipid Nanoparticles for Parental Drug Delivery, Advanced Drug Delivery Reviews, 2004, vol. 56, pp. 1257-1272.
Wang et al., Rapid and Sensitive Liquid Chromatography—Tandem Mass Spectrometric Method for the Quantitation of Metformin in Human Plasma, Journal of Chromatography B, 2004, vol. 808, pp. 215-219.
Wojtera et al., Microglial Cells in Neurodegenerative Disorders, Folia Neuropathologica, 2005, vol. 43, No. 4, pp. 311-321.
Wang et al., Determination of In Vitro Permeability of Drug Candidates Through a Caco-2 Cell Monolayer by Liquid Chromatography/Tandem Mass Spectrometry, Journal of Mass Spectrometry, 2000, vol. 35, pp. 71-76.
Yokoyama et al., Characterization of Physical Entrapment and Chemical Conjugation of Adriamycin in Polymeric Micelles and Their Design for In Vivo Delivery to a Solid Tumor, Journal of Controlled Release, 1998, vol. 50, pp. 79-92.
Siddiqui et al., Introducing Nanochemoprevention as a Novel Approach for Cancer Control: Proof of Principle with Green Tea Polyphenol Epigallocatechin-3-Gallate, Cancer Research, 2009, vol. 69, No. 5, pp. 1712-1716.
Tian et al., Complexation and Release of Doxorubicin from its Complexes with Pluronic P85-b-poly(acrylic acid) Block Copolymers, Journal of Controlled Release, 2007, vol. 21, pp. 137-145.
Sparidans et al., Liquid Chromatograph—Tandem Mass Spectrometric Assays for Salinomycin in Mouse Plasma, Liver, Brain and Small Intestinal Contents and in OptiMEM Cell Culture Medium, Journal of Chromatography B, 2007, vol. 855, pp. 200-210.
Ullmann et al., A Single Ascending Dose Study of Epigallocatechin Gallate in Healthy Volunteers, The Journal of International Medical Research, 2003, vol. 31, pp. 88-101.
Tarkowski et al., Cerebral Pattern of Pro- and Anti-Inflammatory Cytokines in Dementias, Brain Research Bulletin, 2003, vol. 61, pp. 255-260.
Ullmann et al., Plasma-Kinetic Characteristics of Purified and Isolated Green Tea Catechin Epigallocatechin Gallate (EGCG) After 10 Days Repeated Dosing in Healthy Volunteers, Int. J. Vitam. Nutr. Res., 2004, vol. 74, No. 4, pp. 269-278.
Rezai-Zadeh et al., Flavonoid-Mediated Presenilin-1 Phosphorylation Reduces Alzheimer's Disease Beta-Amyloid Production, J. Cell. Mol. Med., 2009, vol. 13, No. 3, pp. 574-588.
Sakamoto et al., Liposome Targeting to Rat Brain: Effect of Osmotic Opening of the Blood-Brain Barrier, Brain Research, 1993, vol. 629, pp. 171-175.
Lin et al., Pharmacokinetics of (−)-Epigallocatechin-3-Gallate in Conscious and Freely Moving Rats and Its Brain Regional Distribution, Journal of Agricultural and Food Chemistry, 2007, vol. 55, pp. 1517-1524.
Meeuwsen et al., Cost-Effectiveness of Post-Diagnosis Treatment in Dementia Coordinated by Multidisciplinary Memory Clinics in Comparison to Treatment Coordinated by General Practitioners: An Example of a Pragmatic Trial, The Journal of Nutrition, Health & Aging, 2009, vol. 13, No. 3, pp. 242-248.
Rao et al., Self-Nanoemulsifying Drug Delivery System (SNEDDS) for Oral Delivery of Protein Drugs III. In Vivo Oral Absorption Study, International Journal of Pharmaceutics, 2008, vol. 362, pp. 16-19.
Liu et al., Formulation of Drugs in Block Copolymer Micelles: Drug Loading and Release, Current Pharmaceutical Design, 2006, vol. 12, pp. 4685-4701.
Pandey et al., Nano-Encapsulation of Azole Antifungals: Potential Applications to Improve Oral Drug Delivery, International Journal of Pharmaceutics, 2005, vol. 301, pp. 268-276.
Rezai-Zadeh et al., Green Tea Epigallocatechin-3-Gallate (EGCG) Modulates Amyloid Precursor Protein Cleavage and Reduces Cerebral Amyloidosis in Alzheimer Transgenic Mice, The Journal of Neuroscience, 2005, vol. 25, No. 38, pp. 8807-8814.
Maeda, The Enhanced Permeability and Retention (EPR) Effect in Tumor Vasculature: The Key Role of Tumor-Selective Macromolecular Drug Targeting, Advanc. Enzyme Regul., 2001, vol. 41, pp. 189-207.
Pattanaik et al., Effect of Piperine on the Steady-State Pharmacokinetics of Phenytoin in Patients with Epilepsy, Phytother. Res., 2006, vol. 20, pp. 683-686.
Italia et al., Nanoparticles Enhance Per Oral Bioavailability of Poorly Available Molecules: Epigallocatechin Gallate Nanoparticles Ameliorates Cyclosporine Induced Nephrotoxicity in Rats at Three Times Lower Dose Than Oral Solution, Journal of Biomedical Nanotechnology, 2008, vol. 4, pp. 304-312.
Khajuria et al., Piperine Modulates Permeability Characteristics of Intestine by Inducing Alterations in Membrane Dynamics: Influence on Brush Border Membrane Fluidity, Ultrastructure and Enzyme Kinetics, Phytomedicine, 2002, vol. 9, pp. 224-231.
Kim et al., Polymer Micelles with Cross-Linked Polyanion Core for Delivery of a Cationic Drug Doxorubicin, Journal of Controlled Release, 2009, vol. 138, pp. 197-204.
Kumar et al., Development and Evaluation of Nitrendipine Loaded Solid Lipid Nanoparticles: Influence of Wax and Glyceride Lipids on Plasma Pharmacokinetics, International Journal of Pharmaceutics, 2007, vol. 335, pp. 167-175.
Feng, Metabolism of Green Tea Catechins: An Overview, Current Drug Metabolism, 2006, vol. 7, pp. 755-809.
Giunta et al., HIV-1 TAT Inhibits Microglial Phagocytosis of ABeta Peptide, Int. J. Clin. Exp. Pathol., 2008, vol. 1, pp. 260-275.
Frezard et al., Enhanced Oral Delivery of Antimony from Meglumine Antimoniate/Beta-Cyclodextrin Nanoassemblies, International Journal of Pharmaceutics, 2008, vol. 347, pp. 102-108.
He et al., Improved Bioavailability of Orally Administered Mifepristone from PLGA Nanoparticles, International Journal of Pharmaceutics, 2007, vol. 334, pp. 173-178.
Giunta et al., EGCG Mitigates Neurotoxicity Mediated by HIV-1 Proteins gp120 and Tat in the Presence of IFN-Gamma: Role of JAK/STAT1 Signaling and Implications for HIV-Associated Dementia, Brain Research, 2006, vol. 1123, pp. 216-225.
Huynh et al., Lipid Nanocapsules: A New Platform for Nanomedicine, International Journal of Pharmaceutics, 2009, vol. 379, pp. 201-209.
Alisky, The Coming Problem of HIV-Associated Alzheimer's Disease, Medical Hypotheses, 2007, vol. 69, pp. 1140-1143.
Bontha et al., Polymer Micelles with Cross-Linked Ionic Cores for Delivery of Anticancer Drugs, Journal of Controlled Release, 2006, vol. 114, pp. 163-174.
Allen, Liposomal Drug Formulations, Rationale for Development and What We Can Expect for the Future, Drugs, 1998, vol. 56, No. 5, pp. 747-756.
Burns et al., Alzheimer's Disease, BMJ, 2009, vol. 338, pp. 467-471.
Bailey et al., Peripheral Biomarkers in Autism: Secreted Amyloid Precursor Protein-Alpha as a Probable Key Player in Early Diagnosis, Int. J. Clin. Exp. Med., 2008, vol. 1, pp. 338-344.
Chan et al., Intestinal Efflux Transport Kinetics of Green Tea Catechins in Caco-2 Monolayer Model, Journal of Pharmacy and Pharmacology, 2007, vol. 59, pp. 395-400.
Bano et al., Effect of Piperine on Bioavailability and Pharmacokinetics of Propranolol and Theophylline in Healthy Volunteers, Eur. J. Clin. Pharmacol., 1991, vol. 41, pp. 615-617.

* cited by examiner sAPP-α ELISA Normalized Values

| Treatment | Sample | BCA Mean | Normalization Multiplier | Treatment Concentration | sAPP-α Mean | Error Propagation | Normalized sAPP-α | Percent Increase over H2O |
|---|---|---|---|---|---|---|---|---|
| EGCG EtOH/H2O | Un26 | 628.536 | 1.052455577 | 25μM | 207.046 | 26.609 | 217.9067175 | 27.48753747 |
| EGCG EtOH/H2O | Un27 | 687.142 | 0.962692164 | 12.5μM | 198.628 | 24.304 | 191.2176191 | 35.91166035 |
| EGCG EtOH/H2O | Un28 | 761.18 | 0.869053599 | 6μM | 159.137 | 29.304 | 138.2985826 | 48.14154436 |
| EGCG EtOH/H2O | Un29 | 713.778 | 0.926767453 | 3μM | 89.678 | 11.312 | 83.11065161 | 225.4766936 |
| EGCG H2O | Un30 | 768.246 | 0.861060414 | 25μM | 198.504 | 21.876 | 170.9239364 | 0 |
| EGCG H2O | Un31 | 817.725 | 0.80895927 | 12.5μM | 173.918 | 19.299 | 140.6925783 | 0 |
| EGCG H2O | Un32 | 681.37 | 0.970647291 | 6μM | 96.159 | 11.501 | 93.35570467 | 0 |
| EGCG H2O | Un33 | 682.903 | 0.968667906 | 3μM | 26.361 | 3.022 | 25.53505466 | 0 |

A

B

METHODS AND COMPOSITIONS FOR IMPROVING BIOAVAILABILITY OF EPIGALLOCATECHIN GALLATE (EGCG)

CROSS REFERENCE TO RELATED APPLICATIONS

This application claims priority to U.S. Provisional Patent Application No. 61/173,058, entitled "Method for Improving Bioavailability of Epigallocatechin Gallate (ECGC) Through the Use of Nanoparticle Vesicles", filed on Apr. 27, 2009, the contents of which are herein incorporated by reference, and U.S. Provisional Patent Application No. 61/172,970, entitled "Method for Enhancing the Therapeutic Action of Epigallocatechin Gallate (ECGC)," filed Apr. 27, 2009, the contents of which are herein incorporated by reference.

STATEMENT OF GOVERNMENT INTEREST

This invention was made with Government support under Grant No. 5K08 MH082642-02 awarded by the National Institute of Mental Health (NIMH); Grant No. R43AT004871 awarded by the National Center for Complementary and Alternative Medicine (NCCAM); Grant No. R21AG031037 awarded by the National Institutes on Aging. The Government has certain rights in the invention.

FIELD OF INVENTION

This invention relates to catechins Specifically, the invention provides compositions and methods of improving the bioavailability of epigallocatechin gallate (EGCG).

BACKGROUND OF THE INVENTION

The β-amyloid peptide (Aβ) is the major constituent of the neuritic plaques that together with the neurofibrillar tangles are physiologic hallmarks of Alzheimer's disease (AD). Aβ, a 39-43 amino acid peptide, is derived from proteolytic cleavage of the amyloid precursor protein (APP), a type I integral membrane protein that is expressed ubiquitously. APP can be processed via alternative pathways; a non-amyloidogenic secretory pathway includes cleavage of APP to soluble APP (sAPP) by a putative α secretase within the sequence of Aβ peptide, thus precluding the formation of Aβ, whereas the formation of the amyloidogenic Aβ peptides is regulated by the sequential action of β- and γ-secretases. As the proportion of APP, processed by β-secretase vs. α-secretase, may affect the amount of Aβ produced, the regulation of these two pathways may be critically important to the pathogenesis of AD. Proteolyic processing of APP can be regulated by activation of various cell-surface receptors coupled to increased activation of second messenger cascades, including phosphatidylinositol hydrolysis, tyrosine phosphorylation, protein kinase C (PKC), protein kinase A, mitogen-activated protein kinase, protein phosphatase 1 and 2B, and calcium.

It has been suggested previously that Aβ toxicity and aggregation involve transition metals, oxidative stress, and accumulation of reactive oxygen species (ROS). It was also shown that Aβ neurotoxicity might be attenuated by numerous antioxidants and iron chelators. Recently, an increasing body of evidence points to a wide array of non-vitamin antioxidants, such as polyphenolic compounds, that can scavenge ROS, chelate transition metals, such as iron and copper and protect cells from oxidative damage. Indeed, (−)-epigallocatechin-3-gallate (EGCG), the major polyphenol isolated from green tea, was shown in several studies to possess neuroprotective effects against a variety of toxic insults and neuronal injuries.

Over the past decade, intense focus has been given to investigating the processes of APP proteolysis and AP metabolism as possible targets for AD therapy (Hardy and Selkoe, 2002). Various synthetic and naturally occurring compounds have been analyzed for their efficacy in the modulation of these pathological events. One such naturally occurring compound achieving worldwide popularity for its therapeutic application is green tea. Green tea contains polyphenolic structures categorized as flavonoids, which are believed to be the active components accounting for the therapeutic properties of green tea. Arguably, one of the most promising green tea compounds being analyzed is (−)-epigallocatechin-3-gallate (EGCG), which has been extensively studied primarily because of its reported anticarcinogenic effects (Lin and Liang, 2000 Moyers and Kumar, 2004). Recently, EGCG has been found to modulate protein kinase C (PKC) activity and to consequently increase secreted levels of sAPP-α (Levites et al., 2002; Levites et al., 2003). Additionally, EGCG has been shown to inhibit various activities of proinflammatory cytokines (Ahmed et al., 2002; Han, 2003; Li et al., 2004). Accordingly, signal transducer and activator of transcription 1 and nuclear factor kB responses are inhibited by EGCG (Han, 2003; Aktas et al., 2004). Elucidation of these molecular actions of EGCG substantiates the compound as a versatile modulator of cellular responses that may contribute to disease pathogenesis.

EGCG treatment leads to a significant reduction in Aβ production as well as decreased Aβ levels and β-amyloid plaques in the brain. These effects are associated with increased generation of α-CTF and sAPP-α and elevated α-secretase cleavage activity, showing that EGCG promotes the nonamyloidogenic α-secretase proteolytic pathway both in vitro and in vivo.

As shown above, epigallocatechin gallate (EGCG) has recently gained the attention of scientists for implementation as a therapeutic agent for the treatment of many diseases. Current research suggests that EGCG has implications as a treatment for Alzheimer's disease and HIV-associated dementia (HAD). The full benefit of EGCG, however, has yet to be fully realized due to its low bioavailability in vivo.

It has been shown that an oral dose of 800 mg/70 kg/day provides approximately 400 ng/ml EGCG in human plasma. The inventors have recently shown that the dose of EGCG (1000-2000 ng/mL) is necessary for promoting APP α-secretase cleavage in SweAPP N2a cells. Using linear approximation, in order to reach plasma concentrations of 1000 ng/ml, an oral dose of about 1800 mg/70 kg/day would be required. From a safety point of view, this dose might be unacceptable for clinical trials. Since the oral EGCG dosage in most clinical trials for cancer therapy is typically not more than 800 mg/day, regimens which enhance EGCG bioavailability, effecting reductions in Alzheimer pathology and cognitive decline at minimum doses of EGCG, are very desirable. Thus, the absolute bioavailability of EGCG is an important issue for oral administration of EGCG to AD clinical trial. It has been previously reported that decreased bioavailability of EGCG is greatly associated with the glucuronidated form, which is largely present in the plasma of treated mice. Recently, these same researchers further showed that piperine, an alkaloid derived from black pepper, enhances the bioavailability of EGCG by inhibiting glucuronidation. Unfortunately the consumption of piperine for enhancing for EGCG bioavailability would likely be precluded by the side-effects conferred by piperine. Thus what is needed is a method and composition of increasing the bioavailability of EGCG that does not need to be administered with other compounds and does not confer any unwanted side effects on the patient.

SUMMARY OF INVENTION

Prevention of amyloidogenic processing of amyloid precursor protein with the use of natural phyotchemicals capable of enhancing alpha-secretase activity is a therapeutic approach for treatment of neurodegenerative diseases including Alzheimer's Disease (AD) and HIV-associated dementia (HAD). The inventors have recently shown promising preclinical results with the use of green tea polyphenol (−)-epigallocatechin-3-gallate (EGCG) in mouse models of both diseases, however the translation into clinical use has been problematic primarily as a result of poor bioavailability and inefficient delivery to the central nervous system (CNS). Importantly, EGCG has been shown to possess potent anti-inflammatory, and antioxidative capacity. The inventors have shown that EGCG is able to modulate the cleavage of amyloid precursor protein (APP) at the $\alpha$-COOH-terminal fragment, thus preventing beta amyloid plaque formation, a hallmark of AD pathology, and common finding in HIV infection.

The inventors found that encapsulation of EGCG into nanoparticle liposomes significantly increases it's neuronal (SweAPP N2a cells) $\alpha$-secretase enhancing ability in vitro by approximately 82% ($P<0.05$) and it's systemic bioavailability in vivo by nearly four-fold. The inventors discovered that total EGCG concentration in blood and brain tissues reached approximately 1000-1300 ng/mL after 4 weeks of treatment at a maximum dose (300 mg/kg).

One embodiment of the present invention relates to a composition for improving the oral bioavailability of EGCG. The composition is a nanoparticle complex comprised of a catechin, preferably EGCG, which is co-solubilized with a lipid carrier to form a nanoparticle complex that is preferably less than 80 nm in size and more preferably between 30 nm and 80 nm in size. The nanoparticle complex is preferably formed of 1 mg of lipid carrier and between about 8 mg and 16 mg of catechin.

A further embodiment of the present invention is a method of increasing the bioavailability of a catechin, preferably EGCG, through the administration of a nanoparticle complex to treat a neurological disease such as Alzheimer's disease or HIV-associated dementia.

In another embodiment of the invention is a composition that is comprised of a catechin, preferably EGCG, encapsulated within a nanoparticle vesicle, preferably a liposome or niosome. The composition is preferably comprised of 1 mg of nanoparticle vesicle and between 8 mg and 16 mg of catechin. Preferably the composition is between 30 nm and 80 nm in size.

A further embodiment of the present invention relates to a method of increasing the bioavailability of a catechin through the encapsulation of the catechin within the nanoparticle vesicle and administering the vesicle containing the catechin to a patient suffering from a neurological disease such as Alzheimer's disease or HIV-associated dementia.

A further embodiment of the present invention includes a composition comprising a catechin, preferably EGCG and a solution of ethanol and water. Preferably the composition is 90% EGCG and 10% ethanol and water solution.

A further embodiment describes a method of increasing the bioavailability of a catechin, preferably EGCG, through the solubilization of the catechin in a solution of ethanol and water and administering it to a patient in need thereof. The patient in need thereof can be suffering from Alzheimer's disease and HIV-associated dementia (HAD), bacterial infection, virus infection, cancer, fatty liver disease, or hyperlipidemia.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
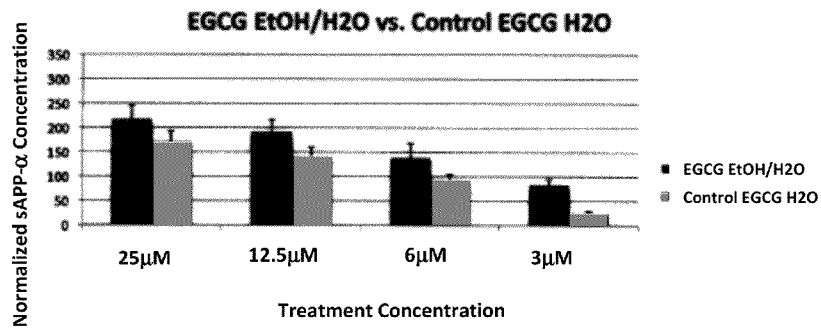
FIG. 1(A) is an ELISA immunoanalysis of EGCG/$H_2O$ versus EGCG/ethanol levels of soluble APP-$\alpha$. (B) is a graph illustrating normalized sAPP-$\alpha$ concentration plotted against treatment concentration for EGCG/$H_2O$ versus EGCG/ethanol.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

"Nanoparticle complex" refers to a composition in which a drug complexes with, but not necessarily encapsulated within, a nanoparticle. The nanoparticle is preferably a lipid carrier. In complexing with the lipid carrier, the drug becomes part of the nanoparticle as opposed to being encapsulated within the nanoparticle. To form the nanoparticle complex of the present invention, a catechin such as EGCG is co-solubilized with a lipid carrier to produce nanoparticle complexes of a particular size, usually between 30 nm and 80 nm but any complex that is equal to or less than 80 nm can be used.

"Lipid carrier" as used herein refers to a nanoparticle that is formed of lipids that is capable of forming a complex with a drug to enhance drug delivery. The lipid carrier can be formed from phospholipids particularly glycerophospholipids, or sterols such as cholesterol.

"Nanoparticle vesicle" as used herein refers to small bubble-like vesicles that may be used as a drug-delivery system. The vesicles may be comprised of lipids such as phospholipids, cholesterol and non-ionic surfactants, copolymers, biodegradable and biocompatible polymers such as chitosin, PLA, PLGA, and starch. Drugs may be encapsulated within the nanoparticle vesicle to enhance bioavailability of the drug. Nanoparticle vesicles include, but are not limited to, liposomes, niosomes, micelles, multilamellar vesicles, unilamellar vesicles, and polymersomes. The nanoparticle vesicles can be between 1 nm and 250 nm (generally over 100 nm) and can encapsulate the drug to be delivered. These vesicles self-assemble during preparation. While the nanoparticle vesicles can range in size, those used in the present invention are preferably between 30 nm and 80 nm so as to be able to pass the blood-brain barrier.

"Neurological disease" as used herein refers to diseases or impairments of the neurological system. The terms "neurological disease" include but are not limited to diseases such as Alzheimer's disease and HIV-associated dementia (HAD) as well as other dementias.

"Patient" is used to describe an animal, preferably a human, to whom treatment is administered, including prophylactic treatment with the compositions of the present invention.

The "therapeutically effective amount" for purposes herein is thus determined by such considerations as are known in the art. A therapeutically effective amount of the compositions of the present invention is that amount necessary to provide a therapeutically effective result in vivo. The amount of composition must be effective to achieve a response, including but not limited to total prevention of (e.g., protection against) and to improved survival rate or more rapid recovery, or improvement or elimination of symptoms associated with neurological diseases such as Alzheimer's disease and HIV-associated dementia (HAD), bacterial infection, virus infection, cancer, fatty liver disease, hyperlipidemia or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process in which the compositions of the present invention are delivered to a patient. The composition may be administered in various ways including oral as well as parenteral (referring to intravenous and intraarterial and other appropriate parenteral routes) among others.

Dosages for the nanoparticle vesicle compositions as well as the nanoparticle complexes preferably consist of a ratio of 1:8, 1:9, 1:10, 1:11, 1:12, 1:13, 1:14, 1:15, and 1:16 with the ratio being 1 mg of nanoparticle vesicle or lipid carrier and between 8 mg and 16 mg of catechin.

Prevention of amyloidogenic processing of amyloid precursor protein with the use of natural phytochemicals capable of enhancing α-secretase activity can be a therapeutic approach for treatment of neurodegenerative diseases including Alzheimer's disease (AD) and HIV-associated dementia (HAD). The inventors have recently shown promising preclinical results with the use of green tea polyphenol, (−)-epigallocatechin-3-gallate (EGCG) in mouse models of both diseases, however the translation into clinical use has been problematic primarily as a result of poor bioavailability and inefficient delivery to the central nervous system (CNS). While the antioxidant properties of EGCG are well known, the inventors have shown that it is able to promote non-amyloidogenic processing of amyloid precursor protein (APP) by upregulating α-secretase, thus preventing brain beta amyloid plaque formation, a hallmark of AD pathology and common finding in HIV infection.

The deterioration, malfunction, or death of neurons is a common etiological factor in several diseases including Alzheimer's disease (AD) and HIV-associated dementia (HAD) (Alisky, 2007; Wojtera et al., 2005). As the number of elderly individuals continues to rapidly increase, neurodegenerative disease, marked by progressive loss of mnemonic and higher cortical functions, has led to a massive socioeconomic burden which is projected to worsen (Tarkowski et al., 2003). Specifically, some 15% of the population greater than 65 years of age suffers from dementia (Meeuwsen et al., 2009). Its presentation is heterogeneous as it is caused by multiple disorders Alzheimer's disease (AD) and vascular dementia (VaD) are the two main causes of dementia affecting between 25-45% and 15-35%, respectively, of all patients suffering from dementia (Burns and Iliffe, 2009). Among dementias where brain infectious viruses are etiologic, human immunodeficiency virus type 1 (HIV-1) associated dementia (HAD) is the most common cause of dementia (Ghafouri et al., 2006).

The inventors have previously shown that modulation of apoptosis cascades (Giunta et al., 2006, 2008), and APP (amyloid precursor protein) processing (Obregon et al., 2006; Rezai-Zadeh et al., 2005, 2009) with the green tea polyphenol, (−)-epigallocatechin-3-gallate (EGCG) can be used as therapy in mouse models of AD and HAD. In spite of these preclinical works, translating them to a human clinical trial has presented problems, primarily as a result of inefficient systemic delivery and bioavailability issues. To achieve maximum response of a neuroprotective agent, novel strategies are required to enhance the oral bioavailability of potentially useful agents. The following examples represent novel strategies to enhance the bioavailability of catechins such as EGCG for the prevention and treatment of various diseases.

Example 1

Epigallocatechin gallate (EGCG) has recently gained the attention of scientists for implementation as a therapeutic agent for the treatment of many diseases. Current research suggests that EGCG has implications as a treatment for Alzheimer's disease, HIV-associated dementia (HAD), bacterium, viruses, as well as many types of cancer. The full benefit of EGCG, however, has yet to be fully realized due to its low bioavailability in vivo.

Many researchers have begun to try to address the bioavailability problems that thwart the development of EGCG as a therapeutic as well as an improved dietary supplement for promoting general health. Although potential methods for altering the pharmacokinetics have been identified, all of them require either the alteration or co-administration of EGCG with other compounds. Implementation of these approaches would, consequently, increase the cost of production and bring about new safety concerns to an otherwise proven-safe, natural compound.

Epigallocatechin gallate has been implicated as a potential target for nutraceutical development due to its antioxidant activity, chemopreventative activity, and its ability to prevent obesity. However, the integration of EGCG into existing products has been slow, some of which can probably be attributed to the high concentration that is required to achieve therapeutic action (because of the low bioavailability in vivo), which consequently increases the cost of production unnecessarily (since most of the EGCG is eliminated from the body).

Although there is a lingering dogma that alcohol consumption negatively impacts one's health, recent research suggests that moderate alcohol consumption can lower the risk of heart disease and is quickly becoming accepted as a way for improving general health and combating some of the problems that commonly arise during aging. The current accepted mechanism for this is that moderate alcohol consumption elevates high-density lipoprotein (HDL or "good cholesterol"). HDL is thought to transport cholesterol that otherwise accumulates in the arteries back to the liver for elimination.

Even though it has already been observed that EGCG shows improved solubility in ethanol solutions, improved solubility does not always correlate with improved bioavailability. This data is the first to show that EGCG in an alcoholic vehicle does display considerable improvements in the bioavailability. Not only this, but it sustains elevated levels of EGCG in the blood over a much longer period of time, when compared to EGCG in $H_2O$ alone. Furthermore, recent research illustrates that EGCG is useful to reverse some of the negative effects of alcohol consumption, including fatty liver disease.

The inventors have discovered that administration of EGCG suspended in an ethanol plus water solution enhances the action of EGCG. Plasma concentrations were measured in rats that were dosed orally with 90% pure EGCG in a 10% ethanol (EtOH) plus water ($H_2O$) solution. As shown in FIG. 1, significant increases in the bioavailability of EGCG occurred when it is delivered in the EtOH vehicle compared to $H_2O$ and EGCG alone. Furthermore, EGCG in EtOH was tested for its ability to promote alpha secretase activity in vitro, using N2A cells that were transfected with the Swedish mutant of APP (swAPP), a common model for Alzheimer's disease. It was found that the EGCG in EtOH showed increased α-secretase activity. Not only was there enhanced α-secretase activity for each concentration that was tested (25 μM-3 μM), but the efficacy of the EGCG/EtOH remained drastically higher than EGCG/$H_2O$ at the low concentration (3 μM). These results illustrate that alcohol enhances the bioavailability of EGCG pharmokinetically and acts in an additive or synergistic pharmodynamic way to reduce the concentration required to achieve therapeutic action.

Previous studies have shown that EGCG can be used not only as a therapeutic for life-threatening diseases, like Alzheimer's, but that it can also be used as a general health supplement, combating age-related oxidative damage, promoting weight loss, preventing the onset of fatty liver disease, and more. Given the increased bioavailability of EGCG in combination with alcohol and water, alcoholic beverages can be the best-suited vehicle for EGCG. Recent studies have shown that alcohol consumption in moderation is can lead to longer life and fewer instances of heart disease. One negative effect of alcohol abuse is fatty liver disease, the accumulation of excess triglycerides inside the liver cells. Recent studies have shown that EGCG can be useful as a therapeutic treatment for people with fatty liver disease. The data shows that the combination of EGCG with EtOH can also be used as a prophylactic for alcohol-related conditions such as fatty liver disease. Both EGCG and EtOH alone have been found independently to improve lipid profiles by reducing LDL and increasing HDL cholesterol blood levels in both animal and human studies. The combination of EGCG and EtOH can be administered to a patient to treat hyperlipidemia based on the enhanced therapeutic action on lipid profiles.

Example 2

Since APP processing occurs at the nanoscale, nanotechnology can be to specifically diagnose and treat neurodegenerative diseases, specifically AD, and HAD. Nanoparticles made up of biodegradable and biocompatible polymers such as chitosin, PLA, PLGA, starch, etc., (Greff et al., 1994) have much evidence to support their safety, biocompatibility, and ability to modulate the chronicity of polymer degradation and thus release of the incorporated compound.

Antioxidants have gained the attention of researchers around the world, both in industry and academia. These compounds are required by the body to scavenge free radicals that would otherwise cause damage at the cellular level. Oxidative stress (caused by an imbalance between oxidants and antioxidants) has been identified as the major cause in many neurodegenerative diseases, cancer, and other age-related diseases. Although humans produce intrinsic enzymatic antioxidants like superoxide dismutase (SOD), catalase (CAT), and glutathione peroxidase, the ability to prevent oxidative damage relies heavily on antioxidants obtained from dietary sources. EGCG is a non-enzymatic antioxidant having the ability to modulate neuroinflammation in Alzheimer's disease (AD) pathology and HIV-associated dementia (HAD).

Figure 2:
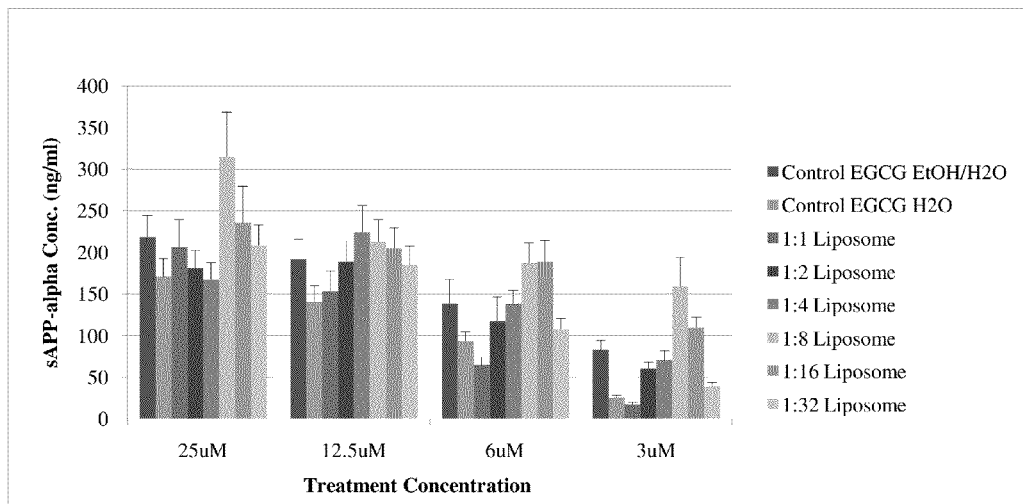
FIG. 2 is a graph of the liposomal formulations against both water and an ethanol control.

The inventors utilized an in vitro model for Alzheimer's disease to test the hypothesis that encapsulation would increase the bioactivity of EGCG by promoting α-secretase activity in cultured SweAPP N2a cells. Additionally, this assay was used as a criterion to select the most effective liposome formulations to carry through to the pharmacokinetic pilot study. FIG. 2 shows a compilation of all of the liposome formulations against both a water and ethanol control. The cell culture assays are well within the water solubility limitations of EGCG. However, the liposomes were prepared for in vivo testing and were much more concentrated in the stock solution. Ethanol was used to solubilize the EGCG and as an important step during the encapsulation process. Therefore, it was appropriate to test the liposomes against an ethanol control to rule out any potential gains in alpha secretase activity being due to the alcohol content of the liposome formulations. According to the percent change in sAPP-α generation in wells with each liposome formulation, the 1:8 and 1:16 formulations were most effective and were chosen for the pharmacokinetic analysis. Not only did these formulations show marked increases in sAPP-α generation but, perhaps more importantly, they continued to promote elevated levels of alpha secretase activity even at the lowest concentration tested 3 uM.

Figure 3:
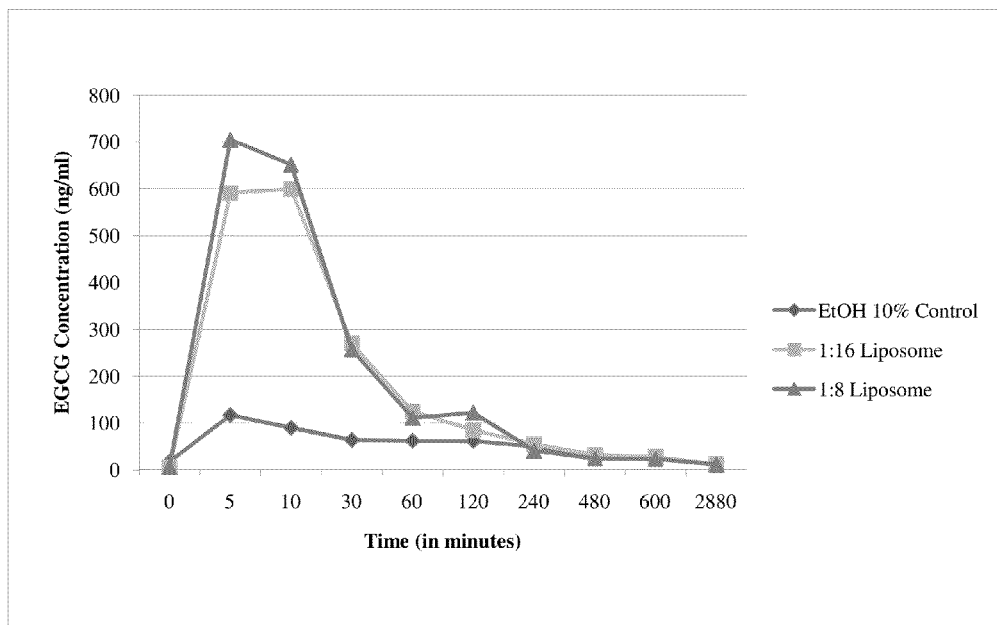
FIG. 3 is a graph of the mean pharmacokinetic curves for each liposome formulation tested and the control.

There have been numerous groups who have reported the very poor oral bioavailability of EGCG. This poor oral bioavailability is mostly due to factors such as poor absorption and intestinal metabolism, rather than elimination via first pass metabolism. Liposomes are widely known to increase the absorption of poorly permeable compounds. The results indicate that encapsulation of EGCG is highly effective at increasing the absorption of EGCG into systemic circulation. FIG. 3 shows a compilation of the mean pharmacokinetic curves for each liposome formulation tested and the control. Because EGCG is poorly water soluble, 10% EtOH was added to fully solubilize the EGCG and ensure accurate dosing in the control. The data shows that the liposome formulations result in drastic increases in absorption of EGCG. FIG. 3 also indicates that both liposome formulations were similar in their effectiveness. The control was very poorly absorbed in comparison. The relative bioavailability (defined by the AUC) of the 1:16 and 1:8 liposomes were 3.89 and 3.62 fold higher than the control, respectively.

Methods

Green tea-derived EGCG (>95% purity by HPLC), was purchased from Sigma Chemical Co. (St Louis, Mo., USA). BCA protein assay kit was purchased from Pierce Biotechnology (Rockford, Ill., USA). Anti-human amyloid-β antibodies 4G8 and 6E10 were obtained from Signet Laboratories (Dedham, Mass., USA) and Biosource International (Camarillo, Calif., USA), respectively.

Liposome preparation was performed as shown in Fountain et al. U.S. patent application Ser. No. 11/644,281, herein incorporated in its entirety by reference.

Murine neuroblastoma cells that were stably transfected with the human APP gene (APP; SweAPP N2a cells) were cultured in 24-well tissue-culture plates at $1 \times 10^5$ cells/well (n=2 for each condition) with 0.5 mL of complete medium (MEM medium with 10% fetal calf serum). Prior to treatment, the MEM was aspirated and replaced with 0.5 mL of neurobasal media and differentiated with cAMP for 4 hrs. Following differentiation, the cells were treated with various liposome formulations and controls (25 uM-3 uM) for 18 hours. The conditioned media was collected and sAPP-α levels quantified using a sAPP-α ELISA kit in accordance with the manufacturers instructions. Additionally, the cell lysate was collected and the total protein content of each well was quantified using a BCA kit in accordance with the manufacturer's instructions.

Male Sprague Dawley rats weighing 200-250 g were purchased from Harlan Laboratories (Indianapolis, Ind.). The rats were purchased pre-cannulated by Harlan. The cannulas had a round tip that was surgically implanted into the jugular vein of the rats making multiple blood draws painless to the animal. The rats were food, but not water, deprived for 18 hours prior to the start of the experiment. The EGCG formulations were delivered via oral gavage at a dosage of 100 mg/kg. Blood was drawn at the following time points: 0, 5, 10, 30, 60, 120, 240, 480, 600, 2880 minutes. Because a small amount of heparin was kept in the catheter lines to prevent clotting, some blood was drawn and discarded before collecting each sample. Approximately 300 µL of blood was collected in EDTA tubes for each time point. The samples were kept on ice to preserve their integrity then centrifuged at 4000 rpm for 10 minutes, afterwhich the plasma was transferred to sterile centrifuge tubes. A preservative solution was added to each plasma sample at 10% (v/v) concentration to ensure the integrity of the EGCG during storage. This preservative was comprised of 20% ascorbic acid (to prevent oxidation of EGCG) and 0.1% EDTA (to scavenge any metal contaminants). The samples were stored at −80° C. until they were analyzed for EGCG content.

The plasma samples were blinded and sent to be analyzed for EGCG content by the Burnham Institute for Medical Research Pharmacology Core (Orlando, Fla.). To most accurately quantify the concentration of EGCG in the plasma, a previously described method was employed using liquid chromatography with tandem mass spectrometry.

Accurately prepared a 2.00 mg/mL stock solution in DMSO of EGCG. The standard spiking solutions were prepared by diluting the stock solution to 1000 µg/mL and 100 µg/mL using acetonitrile:water (1:1, v:v). Both solutions were protected from light using amber vials and all solutions were stored at −20° C.

For this analysis two standard curves were prepared one with a higher (10 µg/ml-0.100 µg/ml) dynamic range the other a lower (1000 ng/ml-10 ng/ml). Both standard curves were prepared using the appropriate blank rat plasma containing the preservative. The results indicated that the standard curve performance was within acceptable range for bioanalytical method acceptance ($R^2 > 0.99$).

Example 3

The inventors investigated the ability of preformulation methods to improve the oral bioavailability of EGCG. It was found that forming nanolipidic EGCG particles improves the neuronal (SweAPP N2a cells) α-secretase enhancing ability in vitro by up to 91% (P<001) and its oral bioavailability in vivo by more than two-fold over free EGCG.

Nanoparticles and larger liposomes have been investigated extensively for increasing the oral bioavailability of poorly absorbed compounds (Frezard et al., 2008; He et al., 2007; Kumar et al., 2007; Pandey et al., 2005; Rao et al., 2008). It has been recently reported that encapsulating EGCG into liposomes can improve its anti-cancer efficacy (Siddiqui et al., 2009) and antioxidant capacity (Italia et al., 2008). However, these studies utilized larger diameter particles (>100 nm) and focused primarily on improved efficacy of EGCG for specific disease modifying parameters. The inventors have tested the ability of small diameter nanolipidic particle formation as a method for increasing not only the α-secretase inducing ability of EGCG, but also its oral bioavailability. These nanoparticles (NanoEGCG) differ from traditional liposomes because they do not require micelle formation. Rather, they are drug:lipid complexes. This enables the formation of smaller diameter particles that are useful for increasing the oral bioavailability of EGCG.

It has been shown that an oral dose of 800 mg/70 kg/day provides approximately 400 ng/ml EGCG in human plasma (Chow et al., 2001). Given that the inventors have recently shown that 1000-2000 ng/mL of free EGCG is necessary for promoting APP α-secretase cleavage in SweAPP N2a cells (Rezai-Zadeh et al., 2005), using linear approximation, an oral dose of EGCG of 1800 mg/70 kg/day would be required to reach therapeutically effective plasma concentrations of EGCG. From a safety and practicality point of view, this dose might be unacceptable for clinical trials (Ullmann et al., 2004, 2003). Since the oral EGCG dosage in most clinical trials for cancer therapy is typically not more than 800 mg/day (Chow et al., 2001) regimens which enhance EGCG bioavailability, effecting reductions in neuropathology and cognitive decline at minimum doses, are very desirable. Thus, the bioavailability of EGCG is an important issue for oral administration of EGCG to clinical trials.

It has been previously reported that decreased bioavailability of EGCG is greatly associated with the glucuronidated form, which is largely present in the plasma of treated mice (Lambert et al., 2003). Additionally, it has been shown that piperine, an alkaloid derived from black pepper, enhances the bioavailability of EGCG by inhibiting glucuronidation (Lambert et al., 2004). Unfortunately the consumption of piperine also influences the metabolism of all other ingested food and drugs (Khajuria et al., 2002). For example it increases the plasma concentration of phenytoin (Pattanaik et al., 2006), propanalol, and theophylline in healthy volunteers (Bano et al., 1991) and plasma concentrations of rifamipicin (Rifampin™) in patients with pulmonary tuberculosis (Zutshi et al., 1985). By forming EGCG nanolipidic complexes, it is possible to increase the oral bioavailability of EGCG as well as its AD and HAD preventative and therapeutic actions, without affecting the absorption of other ingested compounds. This is an important factor to consider when bringing an EGCG therapeutic into the clinical setting.

The inventors modified EGCG such that it requires no co-administration of other drugs. Rather, it is co-solubilized with a lipid carrier using proprietary methodology to form 30-80 nm diameter nanoparticle complexes. The importance of particle diameter for drug delivery is particularly important for delivery of drugs to the brain (Wissing et al., 2004). Previously, even smaller diameter liposomes (100 nm) have had trouble penetrating the tight junctions between the endothelial cells of the blood brain barrier without osmotic disruption (Sakamoto and Ido, 1993). This highlights an important distinction between this nanoparticle technology and previous liposomal technologies, which require micelle formation. NanoEGCG does not involve encapsulating the EGCG into a micelle. Instead, lipid:EGCG complexes are formed. Because the EGCG is not fully encased in a micelle structure, it is possible to achieve smaller diameter particles without compromising the stability of the carrier. While the inventors have demonstrated the ability of nanoparticles to increase the systemic absorption of EGCG taken orally, the small diameter of these particles leads to improved blood brain barrier penetration.

Figures 6, 7:
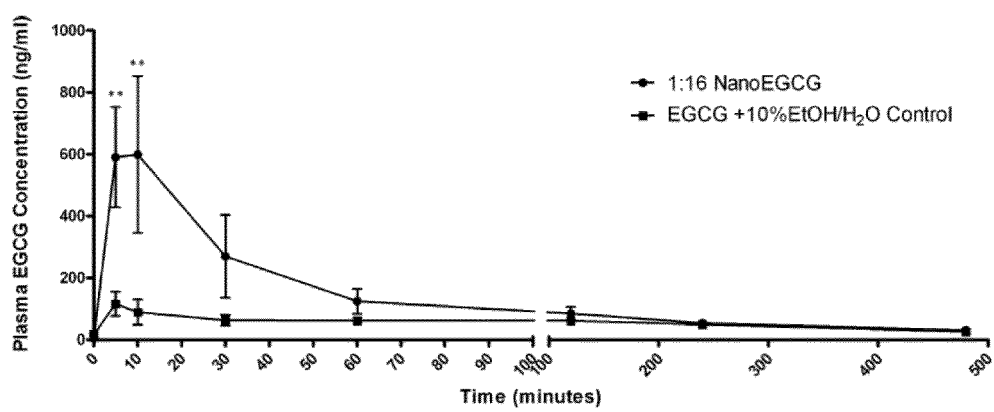
FIG. 6 is a graph illustrating the EGCG pharmacokinetic curve (mean plasma concentration±SEM versus time) for the 1:16 NanoEGCG formulation (n=3) and free EGCG in 10% EtOH solution (n=3). The nanoparticle formulation resulted in substantial increase in systemic EGCG absorption. Statistical significance (**$P<0.01$) was observed at the 5 and 10 min time points. The 10% EtOH control had very poor absorption, with plasma concentration peaking at 116.57 ng/ml. In comparison, the 1:16 NanoEGCG reached a maximum plasma concentration of 599.33 ng/ml.
FIG. 7 is a table of the pharmacokinetic parameters comparing EGCG+10% EtOH, NanoEGCG (1:16), and NanoEGCG (1:8).

Nanolipidic particles are useful for safely translating EGCG into human clinical trials. Not only did NanoEGCG more than double the oral bioavailability of EGCG in rats (FIG. 6) but also was more effective at promoting α-secretase activity in vitro, even at reduced concentrations (FIG. 7). Taken together, NanoEGCG is therapeutically effective at doses that would be considered acceptable in the clinical setting.

Materials and Methods

Reagents and Materials

Green tea-derived EGCG (>95% purity by HPLC) was used for the experiments.

The BCA protein assay kit was purchased from Pierce Biotechnology (Rockford, Ill., USA). Antihuman amyloid-β antibodies 4G8 and 6E10 were obtained from Signet Laboratories (Dedham, Mass., USA) and Biosource International (Camarillo, Calif., USA), respectively.

Preparation of Nanolipidic EGCG Particles (NanoEGCG)

Nanolipidic particles (NanoEGCG) were prepared using a proprietary co-solubilization methodology involving use of monophasic liquid preparations developed by Nature's Defense Systems, Tampa, Fla. The particles were prepared according to the methods described in U.S. patent Ser. No. 11/644,281 to Fountain, herein incorporated in its entirety by reference. As described in Fountain, in preparing the monophasic liquid preparations, a precursor solution is made by solubilizing an amphipathic material in a first quantity of a non-aqueous solvent appropriate to solubilize the amphipathic material to form a first mixture. The amphipathic material may comprise phospholipids (PL) in a mixture of the following phosphatides: phosphatidylcholine (PC), phosphatidylethanolamine (PE), phosphatidic acid (PA) and phosphatidylinositol (PI) at a ratio of PC:PE:PA:PI of 6.5:2.5:0.7:0.3 in ethanol. Preferably, one gram of PL is solubilized in 5.0-7.5 ml of ethanol solvent. After dissolution of the amphipathic material, a quantity of water is added to form a turbid suspension. The amount of water to add is approximately 9 kg to 31 kg of dissolved amphipathic material, but can be varied to result in the desired turbid suspension. A second quantity of non-aqueous solvent, such as ethanol, is added until the turbid suspension is monophasic and has optical clarity at room temperature. This resulting product is a precursor solution which is shelf-stable over time. These particles have a defined size range from 30 to 80 nm. Six nanoparticle formulations were prepared for the study with various ratios of lipid carrier to EGCG. Formulations prepared for this study were 1:1, 1:2, 1:4, 1:8, 1:16, 1:32 (Nanocarrier material to EGCG on a mg/mg basis). To form NanoEGCG co-solubilization methodology involving use of monophasic liquid preparations were employed with proprietary starting materials. These materials are first solubilized into a water-in-ethanol solution (step 1). Anhydrous EGCG was added to the materials in step 1 and co-solubilized by mixing at room temperature (step 2). NanoEGCG particles were formed by the addition of distilled water while mixing materials (step 3). The final preparation of NanoEGCG particles was stirred for an additional 10 min prior to subjecting the preparation to sizing analysis with a Wyatt DynaPro Multiwell Reader (Wyatt Technology Corporation, Santa Barbara, Calif.).

Figure 4:
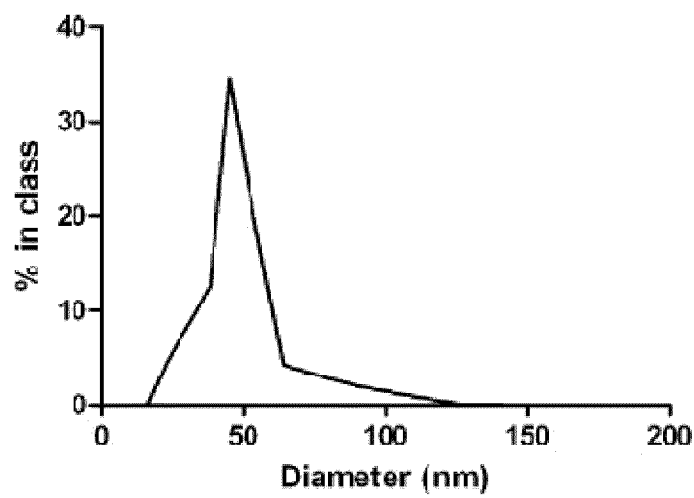
FIG. 4 is a graph illustrating dynamic light scattering data. A Wyatt DynaPro Multiwell Reader was used to characterize the diameter of the NanoEGCG particles. The data indicates a narrow size distribution, with a cumulants mean of 49.5 nm and polydispersity of 0.052.

FIG. 4 shows a representative analysis of the size distribution of the 1:8 NanoEGCG formulation. The stock formulations were stored at 20° C. and protected from light until needed.

Neuronal sAPP-α ELISA

Murine neuroblastoma cells that were stably transfected with the human APP gene (APP; SweAPP N2a cells) were cultured in 24-well tissue-culture plates at 1×105 cells/well (n=2 for each condition) with 0.5 mL of complete medium (MEM medium with 10% fetal calf serum). Prior to treatment, the MEM was aspirated and replaced with 0.5 mL of neurobasal media and differentiated with cAMP for 4 h. Following differentiation, the cells were treated with various nanoparticle formulations and controls (25-3 µM) for 18 h. Controls included two formulations of EGCG without a lipid carrier: one dissolved in water and another in ethanol and water at the same ratio that the nanoparticles were formed (described above). The conditioned media was collected and sAPP-α levels were quantified using a sAPP-α sandwich ELISA protocol as previously described (Bailey et al., 2008). High binding 96-well plates (Nunc, Denmark) were coated with monoclonal antibody 22C11 diluted in 100 µL (1 µg/mL) of carbonate buffer (pH 9.6) and incubated overnight at 4° C. The plate was washed five times with PBS-Tween buffer (0.05% Tween 20) and blocked with 300 µL of blocking buffer (1% BSA and 5% Horse Serum in PBS) for 2 h at 37° C. Synthetic sAPP-α protein (Abgent, San Diego, Calif.) was used as the positive control for this ELISA. All samples were analyzed in duplicate. 100 µL samples of conditioned media were added to each well of the plate. The plate was incubated for 2 h at 37° C. After washing five times, 100 µL of goat anti-human antibody 6E10 (Biosource; diluted 1:3000 in reagent diluent) was added to each well of the plate. Following 2 h-incubation at 37° C. and five times washing, 100 µL of anti-goat IgG conjugated with HRP (1:1500) was added to each well of the plate. The plate was incubated for 1 h at 37° C. Following five times washing, 100 µL of substrate solution (TMB) was added to each well and plate was incubated at room temperature. Twenty minutes later, 50 µL of stop solution (2N H2SO4) was added to each well of the plate. The optical density was determined using a microplate reader at 450 nm. Data were reported as ng of sAPP-α/mg of total intracellular protein produced per well. Total intracellular protein was quantified using a BCA kit (Pierce Biotechnology, Rockford, Ill.) in accordance with the manufacturer's instructions.

Pharmacokinetic Screening of EGCG Formulations in Rats

Male Sprague Dawley rats weighing 200-250 g were purchased from Harlan Laboratories (Indianapolis, Ind.). The rats were precannulated by Harlan. The rounded tip catheters were surgically implanted into the jugular vein of the rats making multiple, precise blood draws painless to the animal. The rats were food (not water) deprived for 18 h prior to the start of the experiment. The EGCG formulations were delivered via oral gavage at a dosage of 100 mg EGCG/kg body weight. Blood was collected at the following time points: 0, 5, 10, 30, 60, 120, 240, and 480 min. Because heparin was kept in the catheter lines to prevent clotting, a small amount of blood was drawn and discarded before collecting each sample. Approximately 300 μL of blood was collected in EDTA tubes for each time point. The samples were kept on ice to preserve their integrity, then centrifuged at 4000 rpm for 10 min, after which the plasma was transferred to sterile centrifuge tubes. A preservative solution was added to each plasma sample at 10% (v/v) concentration to ensure the integrity of the EGCG during storage (Lambert et al., 2006a). This preservative was comprised of 20% ascorbic acid (to prevent oxidation of EGCG) and 0.1% EDTA (to scavenge any metal contaminants). The samples were stored at −80° C. until they were analyzed for EGCG content.

Quantification of EGCG in Rat Plasma

The plasma samples were blinded and sent to be analyzed for EGCG content by the Burnham Institute for Medical Research Pharmacology Core (Orlando, Fla.). To accurately quantify the concentration of EGCG in the plasma, a previously described method was employed using liquid chromatography with tandem mass spectrometry (Sparidans et al., 2007; Wang and Miksa, 2007; Wang et al., 2004, 2000).

Stock Preparation

Accurately prepared a 2.00 mg/mL stock solution in DMSO of EGCG. The standard spiking solutions were prepared by diluting the stock solution to 1000 and 100 μg/mL using acetonitrile:water (1:1, v:v). Both solutions were protected from light using amber vials and all solutions were stored at −20° C.

Standard Curve Preparation

For this analysis two standard curves were prepared one with a higher (10-0.100 μg/ml) dynamic range the other a lower (1000-10 ng/ml). Both standard curves were prepared using the appropriate blank rat plasma containing the preservative. The results indicated that the standard curve performance was within acceptable range for bioanalytical method acceptance ($R^2 > 0.99$) (Sparidans et al., 2007; Wang and Miksa, 2007; Wang et al., 2000).

Pharmacokinetic Calculations

Mean plasma EGCG concentrations±the standard error in the mean (SEM) were calculated using GraphPad PRISM software (GraphPad Software, Inc.). Pharmacokinetic graphs and parameters were determined using GraphPad PRISM. Pharmacokinetic parameters included Cmax, Tmax, area under curve (AUC), and relative bioavailiblity. Relative bioavailability was determined by dividing the AUC of each NanoEGCG formulation by the AUC of the control.

Statistical Analysis sAPP-α ELISA

A two-way ANOVA was performed using GraphPad PRISM software (GraphPad Software, Inc.). This was followed by Bonferonni post-tests to assess the significance of each NanoEGCG formulation versus the EGCG/10% EtOH/H2O control at each concentration.

Pharmacokinetics

A two-way ANOVA was performed using GraphPad PRISM software (GraphPad Software, Inc.). This was followed by Bonferonni post-tests to assess the significance of the 1:16 NanoEGCG formulation versus the EGCG/10% EtOH/H2O control at each time point.

Figure 5:
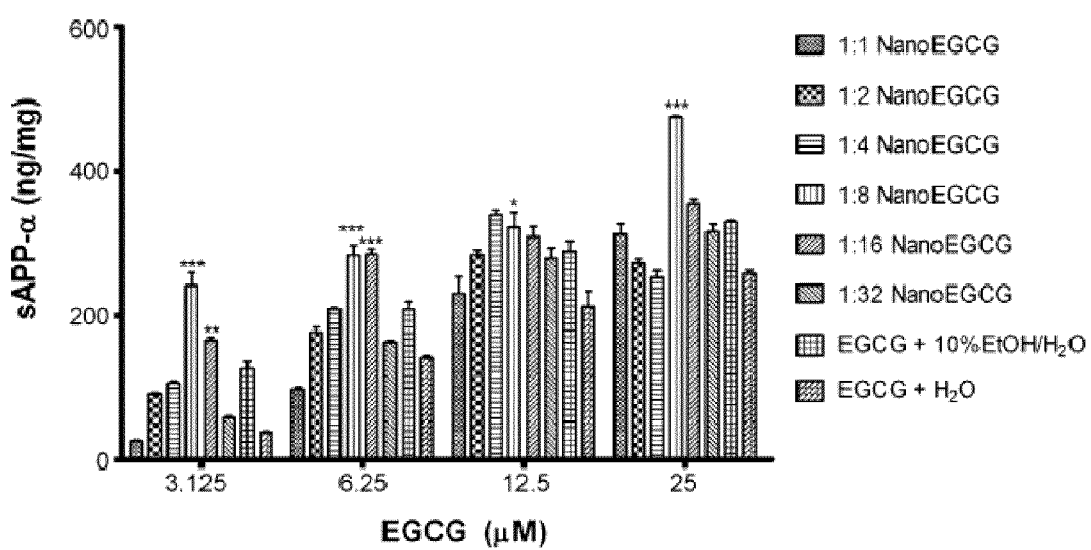
FIG. 5 is a graph illustrating estimated sAPP-$\alpha$ generation for each treatment group. The sAPP-$\alpha$ concentration (ng/ml) was normalized to the total protein content (mg/ml). Data are presented as mean ng of sAPP-$\alpha$ per mg of total protein produced±standard deviation. The 1:8 and 1:16 formulations were superior to the other formulations, with the 1:8 showing 92% improvement in $\alpha$-secretase activity over the EtOH control at the 3 $\mu$M concentration. The 1:8 NanoEGCG formulation was statistically higher than the control at all concentrations tested. The 1:16 NanoEGCG formulation was statistically higher at the lower two concentrations (*$P<0.001$, $P<0.01$, *$P<0.05$).

EGCG Nanoparticle Complexes Increase sAPP-α Generation in Cultured SweAPP N2a Cells The inventors utilized an in vitro model for Alzheimer's disease to show that formation of nanoparticle complexes would increase the bioactivity of EGCG by promoting α-secretase activity in cultured SweAPP N2a cells. These cells overproduce human APP, making them ideal for screening compounds that modulate APP processing (Obregon et al., 2006). FIG. 5 shows the mean ng of sAPP-α per mg of total protein produced±standard deviation for all EGCG formulations. Because ethanol was used to solubilize the lipid carrier and EGCG during the NanoEGCG productions process, it was appropriate to include a similarly formulated EGCG solution (10% EtOH solution v/v) to rule out any potential gains in α-secretase activity being due to the alcohol content of the nanoparticle formulations.

As shown in FIG. 5, not all NanoEGCG formulations were effective. In fact, the 1:1 and 1:2 formulations were outperformed by the EGCG and 10% EtOH/H2O control at all concentrations tested. The 1:8 and 1:16 NanoEGCG formulations were selected to be advanced to the pharmacokinetics phase of the study because they outperformed the control at all concentrations tested. The 1:8 formulation was statistically significant at all concentrations, whereas the 1:16 was only statistically significant at the lower two concentrations. Not only did these formulations show marked increases in sAPP-α generation but, perhaps more importantly, they continued to promote enhanced levels of α-secretase activity even at the lowest EGCG concentration tested.

EGCG Nanoparticle Complexes Improve the Bioavailability of EGCG in Rats

There have been numerous groups to report the poor oral bioavailability of EGCG (Feng, 2006; Cai et al., 2002; Chan et al., 2007; Henning et al., 2008; Lambert et al., 2004, 2006b; Lin et al., 2007; Zhang et al., 2004). Recent reports suggest that this poor oral bioavailability is mostly due to factors such as poor absorption and intestinal metabolism, rather than elimination via first pass metabolism (Cai et al., 2002). Larger lipid-based bilayer delivery systems have been shown to increase the absorption of poorly permeable compounds (Allen, 1998). The inventors evaluated the ability of proprietary lipid nanoparticle complexes to increase the oral bioavailability of EGCG in rats. The results indicate that nanoparticles are highly effective at increasing the absorption of EGCG into systemic circulation. FIG. 6 shows a compilation of the mean pharmacokinetic curves for the nanoparticle formulation tested and the control. Because EGCG is poorly water soluble, 10% EtOH was added to fully solubilize the EGCG at a concentration equivalent to the NanoEGCG stock (50 mg/ml) and ensure accurate dosing in the control. The data shows that the nanoparticle formulations result in substantial increases in the absorption of EGCG. Although FIG. 6 indicates only one NanoEGCG curve, both 1:8 and 1:16 formulations were tested. However, both nanoparticle formulations were similarly absorbed and not statistically different, so the 1:16 preparation was selected to represent the NanoEGCG pharmacokinetic curve. The control was very poorly absorbed in comparison to the NanoEGCG. Statistical significance ($P<0.01$) was observed at the 5 and 10 min time points. FIG. 7** shows some important pharmacokinetic parameters: Cmax, Tmax, AUC, and relative bioavailiblity.

The relative bioavailability (defined by the AUC) of the NanoEGCG was 2.31 and 2.50 for the 1:16 and 1:8 formulations, respectively, in comparison to the free EGCG in 10% EtOH solution (10% EtOH control).

REFERENCES

Alisky, J. M., 2007. The coming problem of HIV-associated Alzheimer's disease. Med. Hypotheses 69, 1140-1143.

Allen, T. M., 1998. Liposomal drug formulations. Rationale for development and what we can expect for the future. Drugs 56, 747-756.

Bailey, A. R., Giunta, B. N., Obregon, D., Nikolic, W. V., Tian, J., Sanberg, C. D., et al., 2008. Peripheral biomarkers in Autism: secreted amyloid precursor protein-alpha as a probable key player in early diagnosis. Int. J. Clin. Exp. Med. 1, 338-344.

Bano, G., Raina, R. K., Zutshi, U., Bedi, K. L., Johri, R. K., Sharma, S. C., 1991. Effect of piperine on bioavailability and pharmacokinetics of propranolol and theophylline in healthy volunteers. Eur. J. Clin. Pharmacol. 41, 615-617.

Bontha, S., Kabanov, A. V., Bronich, T. K., 2006. Polymer micelles with cross-linked ionic cores for delivery of anticancer drugs. J. Control. Rel. 114, 163-174.

Burns, A., Iliffe, S., 2009. Dementia. BMJ 338, b75.

Cai, Y., Anavy, N. D., Chow, H. H., 2002. Contribution of presystemic hepatic extraction to the low oral bioavailability of green tea catechins in rats. Drug Metab. Dispos. 30, 1246-1249.

Chan, K. Y., Zhang, L., Zuo, Z., 2007. Intestinal efflux transport kinetics of green tea catechins in Caco-2 monolayer model. J. Pharm. Pharmacol. 59, 395-400.

Chow, H. H., Cai, Y., Alberts, D. S., Hakim, I., Don, R., Shahi, F., et al., 2001. Phase I pharmacokinetic study of tea polyphenols following single-dose administration of epigallocatechin gallate and polyphenon E. Cancer Epidemiol. Biomarkers Prev. 10, 53-58.

Feng, W. Y., 2006. Metabolism of green tea catechins: an overview. Curr. Drug Metab. 7, 755-809.

Frezard, F., Martins, P. S., Bahia, A. P., Le Moyec, L., de Melo, A. L., Pimenta, A. M., et al., 2008. Enhanced oral delivery of antimony from meglumine antimoniate/betacyclodextrin nanoassemblies. Int. J. Pharm. 347, 102-108.

Ghafouri, M., Amini, S., Khalili, K., Sawaya, B. E., 2006. HIV-1 associated dementia: symptoms and causes. Retrovirology 3, 28.

Giunta, B., Obregon, D., Hou, H., Zeng, J., Sun, N., Nikolic, V., et al., 2006. EGCG mitigates neurotoxicity mediated by HIV-1 proteins gp120 and Tat in the presence of IFN-gamma: role of JAK/STAT1 signaling and implications for HIV-associated dementia. Brain Res. 1123, 216-225.

Giunta, B., Zhou, Y., Hou, H., Rrapo, E., Fernandez, F., Tan, J., 2008. HIV-1 TAT inhibits microglial phagocytosis of abeta peptide. Int. J. Clin. Exp. Pathol. 1, 260-275.

He, W., Horn, S. W., Hussain, M. D., 2007. Improved bioavailability of orally administered mifepristone from PLGA nanoparticles. Int. J. Pharm. 334, 173-178.

Henning, S. M., Choo, J. J., Heber, D., 2008. Nongallated compared with gallated flavan-3-ols in green and black tea are more bioavailable. J. Nutr. 138, 1529S-1534S.

Huynh, N. T., Passirani, C., Saulnier, P., Benoit, J. P., 2009. Lipid nanocapsules: a new platform for nanomedicine. Int. J. Pharm. 379, 201-209.

Italia, J. L., Datta, P., Ankola, D. D., Kumar, M. N. V. R., 2008. Nanoparticles enhance per oral bioavailability of poorly available molecules: epigallocatechin gallate nanoparticles ameliorates cyclosporine induced nephrotoxicity in rats at three times lower dose than oral solution. J. Biomed. Nanotechnol. 4, 304-312.

Khajuria, A., Thusu, N., Zutshi, U., 2002. Piperine modulates permeability characteristics of intestine by inducing alterations in membrane dynamics: influence on brush border membrane fluidity, ultrastructure and enzyme kinetics. Phytomedicine 9, 224-231.

Kim, J. O., Kabanov, A. V., Bronich, T. K., 2009. Polymer micelles with cross-linked polyanion core for delivery of a cationic drug doxorubicin. J. Control. Rel. 138 (3), 197-204.

Kumar, V. V., Chandrasekar, D., Ramakrishna, S., Kishan, V., Rao, Y. M., Diwan, P. V., 2007. Development and evaluation of nitrendipine loaded solid lipid nanoparticles: influence of wax and glyceride lipids on plasma pharmacokinetics. Int. J. Pharm. 335, 167-175.

Lambert, J. D., Lee, M. J., Lu, H., Meng, X., Hong, J. J., Seril, D. N., et al., 2003. Epigallocatechin-3-gallate is absorbed but extensively glucuronidated following oral administration to mice. J. Nutr. 133, 4172-4177.

Lambert, J. D., Hong, J., Kim, D. H., Mishin, V. M., Yang, C. S., 2004. Piperine enhances the bioavailability of the tea polyphenol (−)-epigallocatechin-3-gallate in mice. J. Nutr. 134, 1948-1952.

Lambert, J. D., Lee, M. J., Diamond, L., Ju, J., Hong, J., Bose, M., et al., 2006a. Dose dependent levels of epigallocatechin-3-gallate in human colon cancer cells and mouse plasma and tissues. Drug Metab. Dispos. 34, 8-11.

Lambert, J. D., Sang, S., Hong, J., Kwon, S. J., Lee, M. J., Ho, C. T., et al., 2006b. Peracetylation as a means of enhancing in vitro bioactivity and bioavailability of epigallocatechin-3-gallate. Drug Metab. Dispos. 34, 2111-2116.

Lin, L. C., Wang, M. N., Tseng, T. Y., Sung, J. S., Tsai, T. H., 2007. Pharmacokinetics of (−)-epigallocatechin-3-gallate in conscious and freely moving rats and its brain regional distribution. J. Agric. Food Chem. 55, 1517-1524.

Liu, J., Lee, H., Allen, C., 2006. Formulation of drugs in block copolymer micelles: drug loading and release. Curr. Pharm. Des. 12, 4685-4701.

Maeda, H., 2001. The enhanced permeability and retention (EPR) effect in tumor vasculature: the key role of tumor-selective macromolecular drug targeting. Adv. Enzyme Regul. 41, 189-207.

Meeuwsen, E. J., German, P., Melis, R. J., Adang, E. M., Goluke Willemse, G. A., Krabbe, P. F., et al., 2009. Cost-effectiveness of plost-diagnosis treatment in dementia coordinated by multidisciplinary memory clinics in comparison to treatment coordinated by general practioners: an example of a pragmatic trial. J. Nutr. Health Aging 13, 242-248.

Obregon, D. F., Rezai-Zadeh, K., Bai, Y., Sun, N., Hou, H., Ehrhart, J., et al., 2006. ADAM10 activation is required for green tea (−)-epigallocatechin-3-gallateinduced alpha-secretase cleavage of amyloid precursor protein. J. Biol. Chem. 281, 16419-16427.

Pandey, R., Ahmad, Z., Sharma, S., Khuller, G. K., 2005. Nano-encapsulation of azole antifungals: potential applications to improve oral drug delivery. Int. J. Pharm. 301, 268-276.

Pattanaik, S., Hota, D., Prabhakar, S., Kharbanda, P., Pandhi, P., 2006. Effect of piperine on the steady-state pharmacokinetics of phenytoin in patients with epilepsy. Phytother. Res. 20, 683-686.

Rao, S. V., Yajurvedi, K., Shao, J., 2008. Self-nanoemulsifying drug delivery system (SNEDDS) for oral delivery of protein drugs: III. In vivo oral absorption study. Int. J. Pharm. 362, 16-19.

Rezai-Zadeh, K., Shytle, D., Sun, N., Mori, T., Hou, H., Jeanniton, D., et al., 2005. Green tea epigallocatechin-3-gallate (EGCG) modulates amyloid precursor protein cleavage and reduces cerebral amyloidosis in Alzheimer transgenic mice. J. Neurosci. 25, 8807-8814.

Rezai-Zadeh, K., Douglas Shytle, R., Bai, Y., Tian, J., Hou, H., Mori, T., et al., 2009. Flavonoid-mediated presenilin-1 phosphorylation reduces Alzheimer's disease beta-amyloid production. J. Cell. Mol. Med. 13 (3), 574-588.

Sakamoto, A., Ido, T., 1993. Liposome targeting to rat brain: effect of osmotic opening of the blood-brain barrier. Brain Res. 629, 171-175.

Siddiqui, I. A., Adhami, V. M., Bharali, D. J., Hafeez, B. B., Asim, M., Khwaja, S. I., et al., 2009. Introducing nanochemoprevention as a novel approach for cancer control: proof of principle with green tea polyphenol epigallocatechin-3-gallate. Cancer Res. 69, 1712-1716.

Sparidans, R. W., Lagas, J. S., Schinkel, A. H., Schellens, J. H., Beijnen, J. H., 2007. Liquid chromatography-tandem mass spectrometric assays for salinomycin in mouse plasma, liver, brain and small intestinal contents and in OptiMEM cell culture medium. J. Chromatogr. B: Anal. Technol. Biomed. Life Sci. 855, 200-210.

Tarkowski, E., Liljeroth, A. M., Minthon, L., Tarkowski, A., Wallin, A., Blennow, K., 2003. Cerebral pattern of pro- and anti-inflammatory cytokines in dementias. Brain Res. Bull. 61, 255-260.

Tian, Y., Bromberg, L., Lin, S. N., Hatton, T. A., Tam, K. C., 2007. Complexation and release of doxorubicin from its complexes with pluronic P85-b-poly(acrylic acid) block copolymers. J. Control. Rel. 121, 137-145.

Ullmann, U., Haller, J., Decourt, J. P., Girault, N., Girault, J., Richard-Caudron, A. S., et al., 2003. A single ascending dose study of epigallocatechin gallate in healthy volunteers. J. Int. Med. Res. 31, 88-101.

Ullmann, U., Haller, J., Decourt, J. D., Girault, J., Spitzer, V., Weber, P., 2004. Plasma-kinetic characteristics of purified and isolated green tea catechin epigallocatechin gallate (EGCG) after 10 days repeated dosing in healthy volunteers. Int. J. Vitam. Nutr. Res. 74, 269-278.

Wang, M., Miksa, I. R., 2007. Multi-component plasma quantitation of antihyperglycemic pharmaceutical compounds using liquid chromatography tandem mass spectrometry. J. Chromatogr. B: Anal. Technol. Biomed. Life Sci. 856, 318-327.

Wang, Z., Hop, C. E., Leung, K. H., Pang, J., 2000. Determination of in vitro permeability of drug candidates through a caco-2 cell monolayer by liquid chromatography/tandem mass spectrometry. J. Mass Spectrom. 35, 71-76.

Wang, Y., Tang, Y., Gu, J., Fawcett, J. P., Bai, X., 2004. Rapid and sensitive liquid chromatography-tandem mass spectrometric method for the quantitation of metformin in human plasma. J. Chromatogr. B: Anal. Technol. Biomed. Life Sci. 808, 215-219.

Wissing, S. A., Kayser, O., Muller, R. H., 2004. Solid lipid nanoparticles for parenteral drug delivery. Adv. Drug Deliv. Rev. 56, 1257-1272.

Wojtera, M., Sikorska, B., Sobow, T., Liberski, P. P., 2005. Microglial cells in neurodegenerative disorders. Folia Neuropathol. 43, 311-321.

Yokoyama, M., Fukushima, S., Uehara, R., Okamoto, K., Kataoka, K., Sakurai, Y., et al., 1998. Characterization of physical entrapment and chemical conjugation of adriamycin in polymeric micelles and their design for in vivo delivery to a solid tumor. J. Control. Rel. 50, 79-92.

Zhang, L., Zheng, Y., Chow, M. S., Zuo, Z., 2004. Investigation of intestinal absorption and disposition of green tea catechins by Caco-2 monolayer model. Int. J. Pharm. 287, 1-12.

Zutshi, R. K., Singh, R., Zutshi, U., Johri, R. K., Atal, C. K., 1985. Influence of piperine on rifampicin blood levels in patients of pulmonary tuberculosis. J. Assoc. Physicians India 33, 223-224.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,
What is claimed is:

1. A nanoparticle complex having a size equal to or less than 80 nm comprising:
    a catechin capable of enhancing α-secretase activity; and
    a lipid carrier wherein the lipid carrier is comprised of a monophasic liquid preparation comprised of a mixture of phosphatidylcholine (PC), phosphatidylethanolamine (PE), phosphatidic acid (PA) and phosphatidylinositol (PI);
    wherein the catechin and the lipid carrier are co-solubilized to form the nanoparticle complex in which the catechin is not encapsulated within the nanoparticle complex;
    wherein the complex contains about 1 mg of the lipid carrier and between about 8 mg and about 16 mg of the catechin;
    wherein concentration of the catechin is between about 3 µM and about 6 µM.

2. The nanoparticle complex of claim 1, wherein the catechin is EGCG.

3. The nanoparticle complex of claim 1 wherein ethanol is used to co-solubilize the catechin and the lipid carrier.

4. A method of increasing the bioavailability of a catechin comprising:
    providing a catechin capable of enhancing α-secretase activity;
    providing a lipid carrier wherein the lipid carrier is comprised of a monophasic liquid preparation comprised of a mixture of phosphatidylcholine (PC), phosphatidylethanolamine (PE), phosphatidic acid (PA) and phosphatidylinositol (PI);
    co-solubilizing the catechin and the lipid carrier to form the nanoparticle complex in which the catechin is not encapsulated within the nanoparticle complex and;
    administering the nanoparticle complex to a patient in need thereof;

wherein the complex contains about 1 mg of the lipid carrier and between about 8 mg and about 16 mg of the catechin;
wherein concentration of the catechin is between about 3 μM and about 6 μM;
wherein the nanoparticle complex has a size equal to or less than 80 nm.

5. The method of claim 4 wherein the catechin is EGCG.

6. The method of claim 4 wherein ethanol is used to co-solubilize the catechin and the lipid carrier.

7. The method of claim 4 wherein the patient suffers from a neurological disease selected from the group consisting of Alzheimer's disease and HIV-associated dementia (HAD).

8. A method of increasing the bioavailability of a catechin comprising:
providing a catechin capable of enhancing α-secretase activity;
providing a nanoparticle vesicle comprised of a lipid carrier wherein the lipid carrier is comprised of a monophasic liquid preparation comprised of a mixture of phosphatidylcholine (PC), phosphatidylethanolamine (PE), phosphatidic acid (PA) and phosphatidylinositol (PI);
encapsulating the catechin within the bilayer of the nanoparticle vesicle; and
administering the nanoparticle vesicle containing the catechin to a patient in need thereof;
wherein the nanoparticle vesicle contains about 1 mg of the lipid carrier and between about 8 mg and about 16 mg of the catechin;
wherein concentration of the catechin is between about 3 μM and about 6 μM;
wherein the nanoparticle complex has a size equal to or less than 80 nm.

9. The method of claim 8 wherein the catechin is EGCG.

10. The method of claim 8 wherein the patient suffers from a neurological disease selected from the group consisting of Alzheimer's disease and HIV-associated dementia (HAD).

11. The nanoparticle complex of claim 1, wherein the mixture of phosphatidylcholine (PC), phosphatidylethanolamine (PE), phosphatidic acid (PA) and phosphatidylinositol (PI) is provided at a ratio of PC:PE:PA:PI of 6.5:2.5:0.7:0.3.

12. The nanoparticle complex of claim 1, wherein the mixture of phosphatidylcholine (PC), phosphatidylethanolamine (PE), phosphatidic acid (PA) and phosphatidylinositol (PI) is dissolved in ethanol.

\* \* \* \* \*